(12) United States Patent
Schroeder et al.

(10) Patent No.: US 9,718,741 B2
(45) Date of Patent: Aug. 1, 2017

(54) ORGANIC COMPOUNDS

(71) Applicants: Givaudan, S.A., Vernier (CH); Amyris Inc., Emeryville, CA (US)

(72) Inventors: Fridtjof Schroeder, Hettlingen (CH); Fabian Ruethi, Zurich (CH)

(73) Assignees: Givaudan, S.A., Vernier (CH); Amyris, Inc., Emeryville, CA (US)

( * ) Notice: Subject to any disclaimer, the term of this patent is extended or adjusted under 35 U.S.C. 154(b) by 0 days.

(21) Appl. No.: 15/031,158

(22) PCT Filed: Oct. 24, 2014

(86) PCT No.: PCT/EP2014/072882
§ 371 (c)(1),
(2) Date: Apr. 21, 2016

(87) PCT Pub. No.: WO2015/059290
PCT Pub. Date: Apr. 30, 2015

(65) Prior Publication Data
US 2016/0280615 A1    Sep. 29, 2016

(30) Foreign Application Priority Data

Oct. 25, 2013 (GB) .................................. 1318886.7

(51) Int. Cl.
| | | |
|---|---|---|
| *C07C 261/00* | (2006.01) | |
| *C07C 269/00* | (2006.01) | |
| *C07C 271/00* | (2006.01) | |
| *C07B 37/02* | (2006.01) | |
| *C07C 67/347* | (2006.01) | |
| *C07B 37/08* | (2006.01) | |
| *C07C 2/86* | (2006.01) | |
| *C07C 45/69* | (2006.01) | |
| *C07C 41/30* | (2006.01) | |
| *B01J 31/22* | (2006.01) | |

(52) U.S. Cl.
CPC ........... *C07B 37/02* (2013.01); *B01J 31/2213* (2013.01); *C07B 37/08* (2013.01); *C07C 2/86* (2013.01); *C07C 41/30* (2013.01); *C07C 45/69* (2013.01); *C07C 67/347* (2013.01); *B01J 2231/324* (2013.01); *B01J 2531/824* (2013.01); *C07C 2101/02* (2013.01); *C07C 2102/50* (2013.01); *C07C 2531/22* (2013.01)

(58) Field of Classification Search
CPC ...... C07B 37/02; C07B 37/08; B01J 31/2213; B01J 2231/324; B01J 2501/824; B01J 2531/824; C07C 41/30; C07C 45/69; C07C 2/86; C07C 67/347; C07C 2531/22; C07C 2102/50; C07C 2101/02; C07C 13/04; C07C 43/21; C07C 49/553; 69/608

See application file for complete search history.

(56) References Cited

U.S. PATENT DOCUMENTS

| | | |
|---|---|---|
| 4,650,881 A | 3/1987 | Larock et al. |
| 5,854,405 A | 12/1998 | Archibald et al. |
| 9,073,924 B2 * | 7/2015 | Burgess ............... C07D 471/04 |

FOREIGN PATENT DOCUMENTS

WO    WO 2010/131147 A1    11/2010

OTHER PUBLICATIONS

PCT/EP2014/072882—International Search Report, mailed Apr. 9, 2015.
PCT/EP2014/072882—International Written Opinion, mailed Apr. 9, 2015.
PCT/EP2014/072882—International Preliminary Report on Patentability, issued Apr. 26, 2016.
GB1318886.7—Great Britain Search Report, Apr. 25, 2014.
Arndt, F., "Nitrosomethylurea", Organic Syntheses, 1943, p. 461, vol. 2; 1953, p. 48, vol. 15.
Creary, et al., "Photochemical Behavior of Cyclopropyl-Substituted Benzophenones and Valerophenones", The Journal of Organic Chemistry, Apr. 1, 2011, pp. 2062-2071, vol. 76, No. 1.
Frater, et al., "Synthesis and Olfactory Properties of (−)-(1R,2S)-Georgywood", Tetrahedron Asymmetry, Dec. 13, 2004, pp. 3967-3972. vol. 15, No. 24, Pergamon Press Ltd, Oxford, GB. Abstract Only.
Gagnon, et al., "Palladium-Catalyzed Cross-Coupling Reaction of Tricyclopropylbismuth with Aryl Halides and Triflates", The Journal of Organic Chemistry, May 1, 2008, pp. 3604-3607, vol. 73, No. 9.
Hahn, et al., "Electrical Effects of Cycloalkyl Groups", Journal of the American Chemical Society, Jun. 19, 1968, pp. 3404-3415, vol. 90, No. 13. First page only.
Jones, et al., "The Cyclopropylidene: Generation and Reactions", Jan. 1, 1963, pp. 2754-2759, vol. 85, No. 18. First page only.
Li, Man-Bo, et al., "Cross-Coupling of Grignard Reagents with Sulfonyl-Activated $sp^3$ Carbon-Nitrogen Bonds", Advance Synthesis & Catalysis, Aug. 10, 2011, pp. 1980-1984, vol. 353, Issue 11-12. Absract Only.
Li, Wei-Dong Z., et al., "A Novel Synthesis of Functionalized Allylsilanes", Organic Letters, Apr. 14, 2004, pp. 1849-1852, vol. 6, No. 11.
Mastronardi, F., et al., "Continuous Flow Generation of Reactions of Anhydrous Diazomethan Using a Teflon AF-2400 Tube-In-Tube Reactor", Organic Letters, Oct. 15, 2013, pp. 5590-5593, vol. 15, issue 21. Abstract Only.

(Continued)

*Primary Examiner* — Yevegeny Valenrod
*Assistant Examiner* — Blaine G Doletski
(74) *Attorney, Agent, or Firm* — Curatolo Sidoti Co., LPA; Joseph G. Curatolo; Salvatore A. Sidoti

(57) ABSTRACT

A process of converting a carbon-carbon multiple bond to a cyclopropane ring, comprising the addition of a N-alkyl-N-nitroso compound to a mixture of alkene precursor, aqueous base and Pd(II)-catalyst, with the N-alkyl-N-nitroso compound obtained directly from an alkyl amine derivative, $NaNO_2$ and an acid via phase separation of the N-alkyl-N-nitroso compound from the aqueous phase.

22 Claims, 1 Drawing Sheet

(56) References Cited

OTHER PUBLICATIONS

Matsuda, T., et al., "Activation of a Cyclobutanone Carbon-Carbon Bond over an Aldehyde Carbon-Hydrogen Bond in the Rhodium-catalyzed Decarbonylation", Chemistry Letters, Jan. 1, 2006, pp. 288-289, vol. 35, No. 3. Abstract Only.

Morandi, B., et al. "Iron-Catalyzed Cyclopropanation in 6 M KOH with in Situ Generation of Diazomethane", Science, Mar. 23, 2012, pp. 1471-1474, vol. 335, No. 6075.

Murahashi, et al., Quintet Carbenes m-Phenylenbis (Phenylmethylene) and m-Pheylenebis (Methylene), Tetrahedron, Jan. 1, 1972, pp. 1485-1496, vol. 28. Abstract Only.

Nefedov, et al., "Cyclopropanation of Unsaturated Compounds with Diazomethane Generated in situr, A New Efficient and Practical Route to Cyclopropane Derivatives", Mendeleev Commun., Jul. 3, 1991, pp. 13-15 vol. 1, No. 2.

Ohtake, Y., et al., "5a-Carba-β-D-glucopyranose Derivaties as Novel Sodium-Dependent Glucose Cotransporter 2 (SGLT2) Inhibitors for the Treatment of Type 2 Diabetes", Bioorganic & Medicinal Chemistry, Aug. 3, 2011, pp. 5334-5341, vol. 19, No. 18. Abstract Only.

Ornstein, Paul, et al., "2-Substituted (2SR)-2-Amino-2((1SR,2SR)-2-Carboxycycloprop-1-yl) Clycines as Potent and Selectice Antagonists of Group II Metabotropic Glutamate Receptors. 2. Effects of Aromatic Substitution, Pharmacological Characterization, and Bioavailability", Journal of Medicinal Chemistry, Jan. 29, 1998, pp. 358-378, vol. 41, No. 3. Abstract Only.

Peng, Y., et al., "Revisiting the Corey-Chaykovsky Reaction: the Solvent Effect and the Formation of Beta-Hydroxy Methlthioethers", Tetrahedron, Feb. 6, 2006, pp. 1209-1215, vol. 62, No. 6.

Rossi, et al., "Scalable in Situ Diazomethane Generation in Continuous-Flow Reactors", Organic Process Research & Development, 2012, pp. 1146-1149, vol. 16, No. 5. Abstract Only.

Szabo, G., et al., "Chemical and Biological Investigation of Cycloporpyl Containing Diaryl-Pyrazole-3-Carboxamides as Novel and Potent Cannabinoid Type 1 Receptor Antagnists", Journal of Medicinal Chemistry, Jul. 23, 2009, pp. 4329-4337, vol. 52, No. 14.

Tomilov, Y., et al., "The First Example of the Generation and Trapping of Diazospiropentane by Unsaturated Compounds", Mendeleev Commun. 1997, pp. 200-201, vol. 7. Abstract Only.

Yovell, J., et al., "AIC13-Induced Reactions of Vinylcyclopropanes", Taterahedron, Jan. 1, 1978, pp. 993-996, vol. 34, No. 7. Abstract Only.

Mochalov, et al., "New Pathway to the Synthesis of Substituted 4H-3,1-Benzoxazines," Chemistry of Heterocyclic Compounds, vol. 39, No. 6, 2003. Abstract Only.

Kappe, et al., "Continuous Flow Generation and Reactions of Anhydrous Diazomethane Using a Teflon AF-2400 Tube-in-Tube Reactor," Organic Letters, vol. 15, No. 21, pp. 5590-5593, Oct. 15, 2013. Abstract Only.

Stark, et al., "Continuous Production of the Diazomethane Precurson N-Mehtyl-N-nitroso-p-toluenesulfonamide: Bath Optimization and Transfer into a Microreactor Setup," Organic Process Research & Development, vol. 13, No. 5, pp. 1014-1021, Aug. 31, 2009. Abstract Only.

Black, "The Preparation and Reactions of Diazomethane," Aldrichimica Acta, vol. 16, No. 1, 1983.

Woehl et al., "Scalable in Situ Diazomethane Generation in Continuous-Flow Reactors", Organic Process Research & Development, 2012, pp. 1146-1149, vol. 16, No. 5. Abstract Only.

* cited by examiner

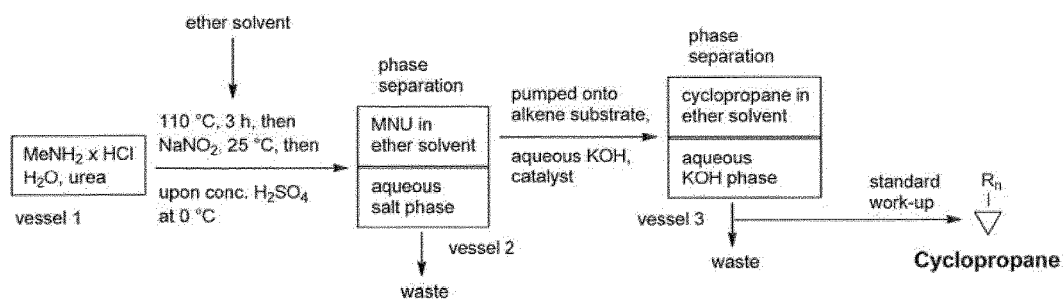

ORGANIC COMPOUNDS

CROSS REFERENCE TO RELATED APPLICATIONS

This application is a national stage application of International Application No. PCT/EP2014/072882, filed 24 Oct. 2014, which claims priority from Great Britain Patent Application No. 1318886.7, filed 25 Oct. 2013, which applications are incorporated herein by reference.

This disclosure relates to a novel process of ring formation across carbon carbon multiple bonds, and in particular cyclopropanation of alkenes. The invention also relates to compounds formed by this process and their use as intermediates in the preparation of useful ingredients such as flavor and fragrance ingredients.

Cyclopropanation, the conversion of a carbon-carbon double bond to a cyclopropane ring, is a chemical transformation used commonly in the synthesis of organic chemical compounds, in particular in the pharmaceutical, agrochemical, and flavors and fragrances industries. Cyclopropanation on a laboratory scale is commonly performed with the aid of diazo compounds, for example, diazomethane (DAM) for methylenation reactions, and transition metal catalysts typically comprising copper or palladium complexes. On a larger, preparative scale relevant to production of commercially-significant quantities of cyclopropanated compounds, diazo compounds are avoided because of safety problems associated with their instability with respect to explosion, as well as their carcinogenicity. Another problem is that diazo compounds are prepared from N-methyl-N-nitroso compounds (MNC's) with the general formula $R(N(NO)Me)_x$ such as N-methyl-N-nitroso-urea (MNU), which are themselves more or less toxic. Ideally, preparation and handling of these compounds should be carried out without exposure of any persons involved in the production process, which is presently difficult to realize due to necessary process operations.

Attempts have been made to avoid the isolation of MNC's as well as DAM, or to facilitate their handling and use, at least.

The substitution of MNU by N-nitroso compounds of lower acute toxicity such as N-methyl-N-nitroso-p-toluenesulfonamide (Diazald™) is well known to chemists (T. H. Black, *Aldrichimica Acta* 16, 3-9, 1983 and references therein). Diazomethane has been generated from Diazald™ in a membrane flow reactor und used for the cyclopropanation of alkenes (O. Kappe et al., Org. Lett. 15, 5590, 2013), however, synthesis and use of Diazald™ requires transportation of the solid compound. Although Diazald™ is less hazardous than MNU, it is still carcinogenic and skin sensitizing (A. Stark et al. OPRD 13, 1014, 2009) and is a self-reacting solid that can undergo explosions by shock, friction, heating and other sources of ignition (P. Woehl, M. Maggini, OPRD 16, 1146, 2012). Transportation and dissolution of solid Diazald™ is also economically not desired due to its high molecular weight.

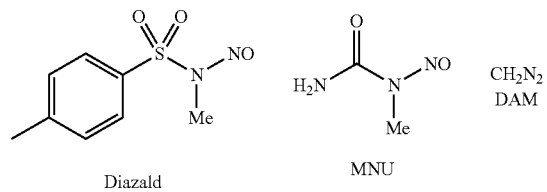

Diazald  MNU  DAM

Nefedov et al. (*Mendelev Communications* 1, 13-15, 1992) have added solid MNU to biphasic mixtures of alkene substrates in methylene chloride or diethyl ether solution, and concentrated aqueous KOH containing palladium-catalysts at 10-20° C. This has the advantage that diazomethane (bp −23° C.) is generated in situ in the reaction mixture and reacts with a reactive alkene substrate before it evaporates. The disadvantage, however, is the isolation, storage and handling of solid MNU, which is problematic for reasons set forth above. Furthermore the addition of hazardous solids to reaction mixtures requires the use of special addition devices, which adds to processing complexity and costs.

Aerojet (U.S. Pat. No. 5,854,405) has claimed a process comprising generation of MNU in organic solvent (a,b), separation of this organic phase from a first aqueous phase (c), contacting the separated organic phase with aqueous inorganic base (d,e) and separation of the thus obtained DAM-containing organic phase from the second aqueous phase (f). Although this process avoids isolation of MNU in solid form, the DAM-containing phase still has to be separated (f) and transported into a reactor where DAM is converted to less harmful products. At this stage, the operators transporting the DAM-containing phase are exposed to the known hazards of this compound.

Loebbecke et al. (*IchemE Symposium Series No.* 153, 1-6, 2007) have addressed this problem by adding MNU, alkene substrate and $Pd(acac)_2$ catalyst in t-butyl methyl ether, diethyl ether or THF to aqueous KOH in a microreactor. Styrene was quantitatively cyclopropanated using this procedure. However, the problem of isolation, handling and dissolving MNU in the solvent was not mentioned by these authors. Also, MNU is rather insoluble in t-butyl methyl ether or diethyl ether (in our hands down to 3% w/w). Accordingly, large quantities of these solvents would be needed to process low quantities of MNU through microreactors rendering the process virtually impractical on large preparative scales.

Woehl and Maggini (*OPRD* 16, 1146, 2012) describe a flow reaction in which MNU 0.5 M in diethyl ether/diethylenglycol (DEG) 1:1 (feed a) is mixed with aqueous KOH (feed b). The thus-produced diazomethane (DAM) is then mixed with excess benzoic acid in ethanol (feed c) to quantitatively convert diazomethane to methylbenzoate. This is an interesting approach, but solid MNU has to be isolated, transported and dissolved in a solvent to provide feed a.

The prior art does not describe processes comprising the synthesis of N-methyl-N-nitroso compounds (MNC's) in organic liquid, and their subsequent reaction with aqueous base in the presence of unsaturated substrates to yield cyclopropanes via in-situ-generated diazomethane. A person skilled in the art is expecting difficulties with such a process, because the MNC is used as unpurified crude and the diazomethane is not separated at all, with the consequence that unreacted starting materials and byproducts such as amines are carried into the cyclopropanation vessel where they could decrease or block the catalyst or decrease its activity in the cyclopropanation reaction. Surprisingly, the applicant has found that exactly such a sequential arrangement of steps resulted in a highly efficient cyclopropanation of unsaturated substrates, especially terminal alkenes.

In case of MNU, for example, its synthesis in situ or in liquid phase and its conversion to diazomethane is attractive for subsequent cyclopropanation reactions, especially under industrial conditions. If prepared from abundantly available urea, methylamine and $NaNO_2$, MNU could be simply converted to ammonium chloride, cyanate, nitrogen and the desired cyclopropanated compound after exposure to base, unsaturated substrate and catalyst. Such a process should produce relatively low amounts of waste materials, provided MNU could be synthesized, worked-up and introduced safely into a cyclopropanation reactor.

The prior art, however, is devoid of any teaching regarding the combination of synthesis and work-up procedures, which is concerned with liquid phase production and safe transfer of MNU into a reactor to mediate in the cyclopropanation of an alkene. On the contrary, the prior art teaches the preparation of MNU in aqueous acidic mixtures, from which it precipitates and is collected by filtration (as described for example in Organikum, VEB Deutscher Verlag der Wissenschaften, Berlin 1986, page 540).

In contradistinction to Nefedov et al (vide infra), applicant has found in a surprising manner that cyclopropanation of alkenes, and in particular terminal alkenes, proceeds readily without organic solvent, or only negligible amounts of organic solvent, for the alkene substrate. By "negligible amounts" is meant, less than 100 weight equivalents of solvent/catalyst, more particularly less than 50 weight equivalents of solvent/catalyst, still more particularly less than 25 weight equivalents of solvent/catalyst or no solvent/catalyst.

In particular, applicant found that when solid MNU was added portion-wise to a stirred mixture of catalyst, terminal alkene (without organic solvent) and aqueous KOH at 5° C., cyclopropanation of the terminal alkene took place efficiently.

This surprising finding renders it possible to industrialize MNU-mediated chemistry to effect ring formation across carbon-carbon multiple bonds, and in particular to cyclopropanate alkenes, and more particularly to cyclopropanate terminal alkenes. The discovery that dissolving an alkene substrate in an organic solvent was not critical for efficient cyclopropanation to occur, enabled the applicant to utilize solvent (that would otherwise be used to dissolve the alkene substrate) as a medium in which to dissolve MNU and to transfer it cleanly and safely into a reaction flask containing the alkene substrate. In this manner, it was possible to avoid handling of the solid toxic solid material.

In a first aspect of the invention there is provided a process of ring formation across a carbon-carbon multiple bond, the process comprising the steps of reacting a N-alkyl-N-nitroso compound in liquid phase with a substrate bearing a carbon-carbon multiple bond, wherein the N-alkyl-N-nitroso compound is generated in liquid form or in an organic phase, which has been separated from an aqueous phase, and the organic phase is added to the unsaturated substrate.

The process of the present invention is useful to convert an alkene or an alkyne to a cyclopropane ring or a cyclopropene ring respectively. Beside N-methyl-N-nitroso compounds (MNC's), one can employ other N-alkyl-N-nitroso compounds, wherein the alkyl group is ethyl, or higher alkyl groups such as propyl, butyl or higher alkyl groups, which may be linear or branched and may be substituted or unsubstituted, such as N-ethyl-N-nitroso urea, N-butyl-N-nitroso urea, 4-(ethylnitrosoamino)-4-methyl-2 pentanone (CAS 5569-45-9) or N-nitroso-N-2-propyn-1-yl-acetamid (CAS 90927-84-7). In order to illustrate the invention however, in the remainder of the specification, reference will mainly be made to MNC's and to reactions concerned with the methylenation of alkenes.

In general, the N-alkyl-N-nitroso compound is generated in-situ or in liquid phase from a mixture of an HNRR' compound, water, NaNO$_2$ and an acid. The MNC's are generated in liquid phase from an aqueous mixture comprising a methyl amine or a derivative of a methylamine, NaNO$_2$, and an acid. An organic solvent can be added to the MNC once it is formed to facilitate phase separation. In particular, MNU may be generated in liquid phase from an aqueous mixture comprising methylurea, NaNO$_2$, and an acid. Alternatively, instead of using methylurea, one can generate this using methylamine or its salts, and urea.

Once the MNC is formed, it partitions into the organic solvent provided for that purpose. A biphasic mixture is formed, and the organic phase can be separated from the aqueous phase in a phase separation step. Thereafter, the organic phase containing the MNC is added to an alkene substrate, without having first to isolate the MNC in pure form. As the MNC is in an organic solvent, it can be cleanly and simply transferred into a reaction vessel containing the alkene substrate.

Suitable N-Methyl-N-nitroso compounds (MNC's) in organic liquid phase are such which can be easily prepared as such from inexpensive components and comprise preferably but not limiting MNC's such as N-methyl-N-nitroso urea (MNU), ethyl N-Methyl-N-nitroso urethane (nitroso-EMU) or N-nitroso-β-methylaminoisobutyl methyl ketone (NMK).

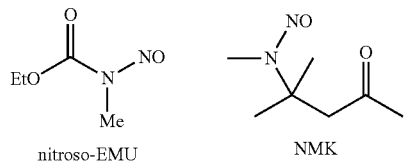

nitroso-EMU   NMK

The term "N-methyl-N-nitroso compound generated in organic liquid phase" includes the generation of N-alkyl-N-nitroso compounds as organic liquid phase, such as nitroso-EMU or NMK. Alternatively, a N-alkyl-N-nitroso compound, which can exist in solid form, can be dissolved in an organic liquid phase.

In a particular embodiment of the present invention there is provided a process of converting a carbon-carbon double bond to a cyclopropane ring, comprising the steps of:
I) generation of the MNC in a biphasic mixture,
II) separation of the organic MNC-containing liquid phase from an aqueous phase and
III) transferring the organic MNC-containing liquid phase into a mixture comprising an alkene substrate, aqueous base and catalyst, thereby to cyclopropanate the alkene substrate.

In a particular embodiment of the invention, the MNC in organic liquid phase is of lower density than the aqueous phase in order that it will float above the aqueous phase and allow the lower aqueous phase to be removed efficiently under gravity in a phase separation step. The addition of solvent or solvent mixtures can enhance this effect.

Suitable solvents for phase separation are polar ethers such as tetrahydrofurane (THF), 2-methyl-tetrahydrofurane (MeTHF), dimethoxyethane (DME), dimethylisosorbide (DMIS), dioxane, or mixtures of these ethers with other co-solvents, which will still allow phase separation to occur between the aqueous phase and the organic phase.

Although ethers are particularly suitable organic solvents for phase separation, also other solvents can be employed, particularly toluene in case of nitroso-EMU or amide-type solvents such as N-Methyl-2-pyrrolidone (NMP) in case of MNU. However, solutions of MNU in N-alkylpyrrolidones or similar amide solvents are inherently unstable due to the basic properties of these solvents. Indeed, MNU will decompose in basic solvents to diazomethane. If these solvents are to be employed, they are best employed in reactions in which a high stationary inventory of MNU in solvent is not generated. For example, the amide solvents can be particularly effective for use in flow chemistry, wherein only very small amounts of MNU in solvent is formed before it is immediately consumed by reacting with an alkene substrate.

The process described herein carried out under flow conditions in a flow reactor represents a further aspect of this invention.

Whereas, it is in particular known in the art to produce MNU from $NaNO_2$, methylamine, urea and an acid (e.g. in the presence of concentrated sulphuric acid), the reaction is carried out expressly to form MNU as a solid and to isolate it from the liquid phase by filtration. In contradistinction, the means by which MNU is isolated in the present invention is by phase separation into a suitable organic solvent. Phase separation is effected when a suitable organic solvent is added to the aqueous phase. The organic solvent may be introduced either before or after addition of the acid (e.g. sulphuric acid), although addition of the organic solvent before acidification avoids the possibility of any precipitation of solid MNU, which would have to be subsequently dissolved.

Considering that the organic solvent has to be polar in order to promote the partitioning of MNU into the organic phase, it was surprising that a good separation between the organic and aqueous layers could be achieved. Good separation is important if the phase separation step is to be carried out efficiently and with the assurance that significant amounts of MNU are not left in the aqueous phase, which is collected as waste. Accordingly, in a preferred embodiment salts are added to the biphasic mixture before phase separation is undertaken. Inorganic and organic salts or salt mixtures may be added to enhance phase separation and extraction of MNU into the organic phase. Furthermore, water, organic solvents and ionic liquids may be added to avoid undesired precipitation of the reaction components during processing.

MNU is readily obtained from stoichiometric amounts of methylamine hydrochloride, urea, $NaNO_2$ and sulphuric acid, or any other organic or inorganic acid and mixtures of acids. These compounds may be mixed in different ratios but ideally between 1:1:1:<1 and 3:3:1:<1. For the purpose of ease of subsequent phase separation and cyclopropanation the ratio may be more particularly 2:2:1:<1.

In an alternative embodiment, when instead of employing methylamine hydrochloride and urea, one uses directly methylurea, the ratio of alkyl urea, $NaNO_2$ and sulphuric acid may be between 1:1:<1 and 3:3:<1. For the purpose of ease of subsequent phase separation and cyclopropanation the ratio may be more particularly 2:2:<1.

A variety of transition metal catalysts can be employed in a process according to the present invention, although palladium catalysts are particularly useful. Examples of suitable catalysts are described by Nefedov et al. in *Izvestiya Akademii Nauk SSSR, Seriya Khimicheskaya* 8, 1861-1869 (1989). Palladium catalysts, e.g. $Pd(acac)_2$, $Pd(OAc)_2$ or $PdCl_2$ are particularly useful when ethylene and mono- or disubstituted alkene substrates are to be cyclopropanated. The mono- or di-substituted alkene substrates may be substituted with any desirable substituents, including but not limited to alkyl or aryl (both of which may be substituted, branched or strained, and include heteroatoms such as nitrogen, oxygen, sulphur or boron) or a carbonyl group (such as in esters, ketones or aldehydes).

The amount of catalyst employed in a process according to the present invention may be less than 0.5%, 0.1 mol %, less than 0.05 mol % and preferably 0.02 mol % or less. Thus in a particular embodiment of this invention Pd-catalysts are used in lower amounts than in the prior art, which describes lowest amounts of 0.06 mol % $Pd(P(OMe)_3)_4$ for the in situ cyclopropanation of a strained alkene (Nefedov, vide supra 1992).

The fact that the applicant was able to carry out a highly efficient transition metal catalysed cyclopropanation was surprising. A potential problem of using MNC's isolated by phase separation from an aqueous layer is that impurities such as amines or inorganic salts may be carried over into the organic phase and into the cyclopropanation vessel containing alkene substrate and transitional metal catalyst. However, whereas it is well known that such impurities can impair the efficiency of transition metal catalyzed reactions, as pointed out by Nefedov (vide supra, 1989) for example, applicant did not encounter any impairment.

FIG. 1 is a schematic representation of a specific embodiment that illustrates the process according to the invention. In a first reaction vessel MNU-precursor I is formed from a mixture of $NaNO_2$, methyl amine and urea in an aqueous medium. An organic solvent is added to this aqueous phase and the whole is pumped onto concentrated acid in a second vessel where after elimination of water, MNU is formed. Alternatively the organic solvent can be added at this stage. Phase separation is carried out in the same vessel (2). The lower aqueous salt solution phase is drained off to waste, whereas the upper organic layer containing the generated MNU is pumped into a third vessel containing the alkene substrate, aqueous basic phase and catalyst. The cyclopropanation reaction proceeds as the two phases are mixed with vigorous stirring, and after the reaction is complete the organic phase containing the cyclopropanated alkene is recovered.

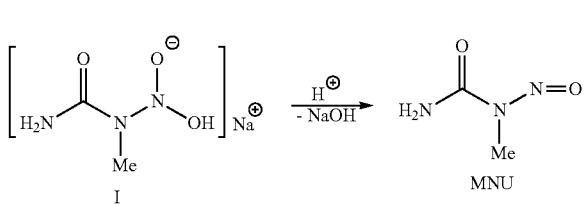

As the acid quench of MNU precursor I in vessel 2 is highly exothermic and the cyclopropanation in vessel 3 is also temperature sensitive, cooling is preferably used for these two steps. In a first aspect, uncontrolled decomposition of MNU needs to be avoided, which might occur above 20° C. and produces methyl isocyanate (MIC). Furthermore, the cyclopropanation is preferably carried out at lower temperature, to avoid release of the low-boiling diazomethane (bp=−23° C.) into the atmosphere and/or dimerization of this reagent to ethylene and nitrogen, which decreases the efficiency of the cyclopropanation step. Both steps are therefore preferably carried out under cooling, e.g. at −20 to +10° C., more preferably around 0° C. These temperatures are nevertheless easily maintained and controlled by the addition rate of MNU precursor I to the acid (step 1) or the addition rate of MNU to the alkene substrate. In flow reactors it should be possible to use higher reaction temperatures.

This set up is relatively non-complex and has the considerable advantage that it avoids separation and handling of solid MNU and reduces human exposure to MNU and diazomethane to a minimum as MNU is generated only in vessel 2 and destroyed (by cyclopropanation) in vessel 3. Furthermore some steps of the reaction sequence can be run in flow reactors, e.g. the MNU generation step (vessel 2), and the phase separation step can be automated.

As in case of the cyclopropanation reaction with MNU any unreacted diazomethane (DAM) can be quenched after the reaction is complete, by the addition of a sacrificial alkene with high reactivity (such as ethylene, styrene, limonene, myrcene or farnesene) or alternatively or additionally, acetic acid or other carboxylic acids, which in the presence of a strong base will decompose any diazomethane by methylation of the acid.

It is preferred that the MNC immediately and completely reacts to DAM, and that DAM immediately and completely reacts with the unsaturated substrate in the reaction mixture, and that these compounds (MNC and/or DAM) are not detectable during and after complete addition of the MNC (in vessel 3). It is therefore preferred that the stationary concentration of both compounds (MNC and/or DAM) is kept at <10%, <5%, <1%, <0.1% and ideally at 0% versus alkene substrate and cyclopropanated product in the reaction mixture. Such a low or close to zero concentration of MNC or DAM (in vessel 3) prevents release of MNC into the environment in case of a reactor damage and thus prevents a spill of a toxic reaction mass. It also prevents release of DAM from the reaction mixture into the headspace of vessel 3 and beyond the confinements of the reactor. In particular, in case of MNC, a low or close to zero concentration of DAM also prevents the formation of other hazardous products, e.g. methylation of the waste product potassium isocyanate to give the highly toxic methyl isocyanate (MIC).

To avoid a stationary concentration of MNC and/or DAM the skilled chemist will adjust the reaction parameters as described above, namely catalyst concentration, temperature and MNC/alkene substrate/cyclopropanated product ratios. It may be of advantage to add a sacrificial alkene with slightly lower reactivity than the target alkene. This sacrificial alkene can be covalently attached to the target alkene (as in any polyene). Alternatively, substoichiometric amounts of MNC versus the alkene substrate may be used. Thus, MNC would be completely consumed and DAM formation would be stopped before the target alkene is completely cyclopropanated. The skillful combination of reaction parameters and ratios of catalysts and reactants guarantee a close to zero stationary concentration of MNC and/or DAM during and after complete MNC addition.

The process according to the present invention can be used to cyclopropanate all mono- and disubstituted alkene substrates as well as ethylene. Preferred, however, are terminal (monosubstituted) alkenes, i.e. those alkenes wherein $R^2$ is H. $R^1$ may be an alkyl, alkylidene, or aryl, which may be branched or unbranched and substituted or unsubstituted. Other preferred alkenes are exo-methylene compounds (i.e. those in which $R^1$ and $R^2$=alkyl, alkylidene or aryl, which may be branched or unbranched and substituted or unsubstituted).

In terminal non-activated isoprenes, wherein $R^3$ is alkyl, alkylidene, or aryl, which may be branched or unbranched and substituted or unsubstituted, first the terminal and then the exo-methylene double bond will react.

Terminal isoprenoid compounds, with one or more tri-substituted double bonds in the substituent $R^3$, are cyclopropanated with high selectivity at the monosubstituted double bond or are double-cyclopropanated at the terminal isoprene unit depending on the reaction conditions. This provides a selective access to mono- or bis-cyclopropanated Myrcene, Farnesene or higher polyprenoid derivatives. Especially the vinylcyclopropanes (monocyclopropanated) are valuable intermediates for further transformations e.g. to flavor & fragrance compounds or their precursors, e.g. pseudo-Georgywood.

In another aspect of the present invention there are provided cyclopropanated isoprenes according to the formula IIIa

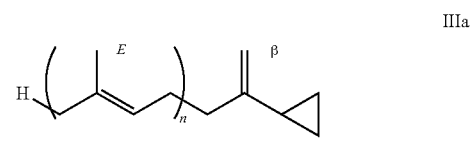

in which n=0, 1, 2 or 3.

In a particular embodiment of the present invention there is provided a cyclopropanated isoprene, myrcene, or farnesene. Depending on the E/Z- and α,β-purity of the polyprene, different double bond isomers or isomer mixtures II can be used as starting material giving after cyclopropanation III.

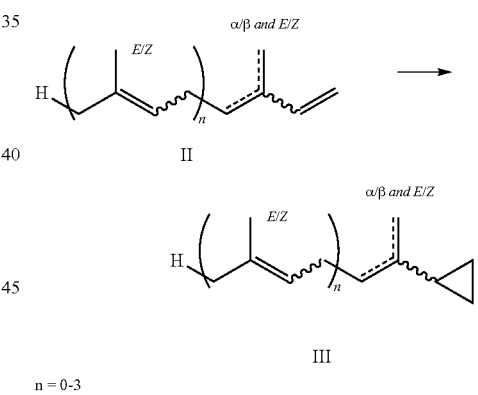

n = 0-3

In a particular embodiment of the present invention there are provided mono- or bis-cyclopropanated myrcenes of the formulae 1 or 2, or a mono-cyclopropanated ocimene of the formula 3.

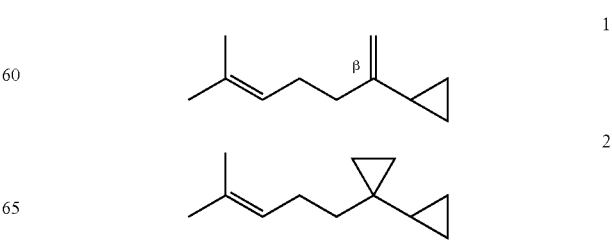

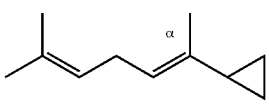

In another particular embodiment of the present invention there are provided mono- or bis-cyclopropanated β-farnesenes of the formulae 4 or 5, or a mono-cyclopropanated α-farnesene of the formula 6.

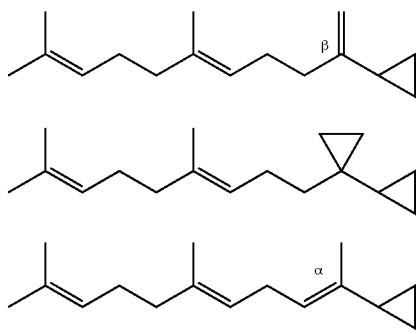

It is known from the literature that cyclopropanation of monosubstituted alkenes is commonly performed with the aid of diazo compounds, such as diazomethane (DAM) for methylenation, and transition metal catalysts, typically comprising palladium complexes. Useful information regarding the transition-metal catalyzed selective methylenation of the monosubstituted double bond in polyenes such as II to monocyclopropanated polyenes such as III, however, is scarce and limited only to precursor isoprene (n=0 in II and III). Although the selectivities towards III (n=0) are relatively good, no hint was given how to improve selectivities and reaction conditions further, e.g. using less catalyst and/or DAM generated in situ in the reaction vessel. The reaction was also not tested on higher polyenes II (with n≥1), probably because more complex mixtures were expected in case of a higher degree of unsaturation. The selective methylenation of polyenes II (with n≥1) has not been reported so far. Compounds III with n≥1 are therefore either unknown, or have been synthesized by more complex routes. A simple access to such compounds (III, n≥1) is nevertheless strongly desired, due to the value of these products in further reactions to useful fragrance compounds.

In another particular embodiment of the present invention there are provided substituted meta- or para-substituted cyclopropylbenzenes of the general formula IV in which R' is a branched or unbranched $C_1$-$C_5$ alkyl radical with n=0, 1 or 2 located in the 1- and/or 2-position of the cyclopropane, and R" is a $C_3$-$C_{10}$ radical, optionally substituted, unsaturated, which contains optionally one or more heteroatoms, carbonyl groups, imines, alcohols, acetals.

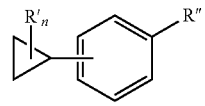

The substituted cyclopropylbenzenes IV can give, after appropriate chemical transformation and purification, as known to the skilled chemist, fragrance compounds of the floral and preferably of the Lilly of the Valley family.

The vinylcyclopropanes of the general formula V can be transformed by vinylcyclopropane rearrangement, known to the chemist skilled in the art, to useful precursors of known fragrance compounds, e.g. using the Rh(I)-catalyzed cycloaddition of vinylcyclopropanes as described by P. Kraft in Synthesis, 695, 1999 and references therein. The cycloaddition products VI give after further transformation valuable fragrance products of the woody-amber family.

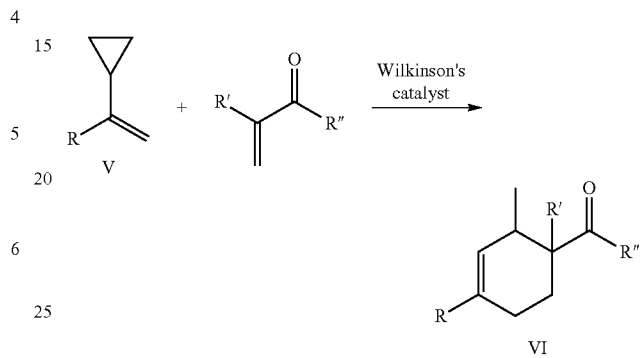

Application of this method to monocyclopropanated myrcene 1 for example gives homomyrcene 10 and pseudo-Georgywood 12 which are both valuable precursors of Georgywood™ depending on the exact reaction conditions.

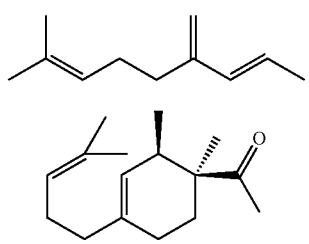

Cyclopropanes generated by the method of the present invention can be also used directly as fragrance compounds, e.g. without further derivatization, such as Δ-Myrcenol 13 and $Δ_2$-Myrcenol 14:

There now follows a series of examples that further act to illustrate the invention.
General Analytical Conditions:
Non-polar GC/MS: 50° C./2 min, 20° C./min 200° C., 35° C./min 270° C. GC/MS Agilent 5975C MSD with HP 7890A Series GC system. Non-polar column: BPX5 from SGE, 5% phenyl 95% dimethylpolysiloxane 0.22 mm×0.25 mm×12 m. Carrier Gas: Helium. Injector temperature: 230° C. Split 1:50. Flow: 1.0 ml/min. Transfer line: 250° C. MS-quadrupol: 106° C. MS-source: 230° C.

Example 1. Preparation of MNU in THF

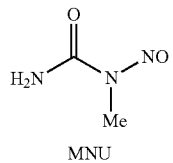

MNU

A solution of urea (175 g, 2.9 mol) and methylamine hydrochloride (198 g, 2.9 mol) in water (400 ml) is heated at reflux (105° C.) for 3.5 h under stirring. At 40° C. NaNO$_2$ (101 g, 1.45 mol) dissolved in water (200 ml) is added. After 15 min THF (1000 ml) is added which results in a transparent 2-phase mixture. Conc. H$_2$SO$_4$ (110 g, 1.1 mol) is added at 0-5° C. and stirring within 1.5 h. After another 0.5 h at 0-5° C. the two transparent phases are separated at 25° C. The organic phase (A, 1065 ml, theoretically 1.35 M) is stored for a few days at 0-5° C. or forwarded immediately to the cyclopropanation reactor.

The water phase is extracted twice with THF (2×1 l). This gives 1100 ml of phase B and 1075 of phase C. Whereas phase A gives a 51% conversion of a terminal alkene to a cyclopropane in a subsequent cyclopropanation reaction, phase B gives <0.5% cyclopropane and phase C gives no detectable conversion. We conclude that >99% MNU are extracted after the first phase separation. Usually the water phase is therefore discarded after the first phase separation (from organic phase A) after treatment with conc. aqueous KOH and acetic acid.

Example 2. Preparation of N-Nitroso-Dimethylurethane in Toluene

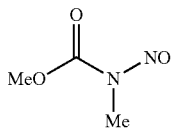

N-Nitroso-dimethyl urethane

H$_3$PO$_4$ 50% in water (9.2 g, 48 mmol) is added to dimethylcarbamate (4.9 g, 55 mmol) at 10-20° C. under stirring. To the colorless 2-phase mixture is added NaNO$_2$ 30% in water (20.1 g, 67 mmol) at 10-15° C. over 1-1.5 h. Nitrous gases are formed at the end of the addition and the orange solution is stirred for 17 h at 25° C. Nitrogen is bubbled through the reaction mixture to expel remaining nitrous gases. Stirring is stopped and a sample is taken from the orange organic layer for analytical analysis which shows a conversion of 88-92% according to GCMS and NMR. The reaction mixture is extracted twice with toluene (15 ml, 10 ml) to give 30 ml of a clear light orange solution which is used as such in the cyclopropanation step.

Analytical data of the organic layer before toluene addition: $^1$H-NMR (CDCl$_3$, 400 MHz): 4.1 (s, 3H), 3.2 (s, 3H) ppm. $^{13}$C-NMR (CDCl$_3$, 400 MHz): 154.2 (s), 54.9 (q), 28.0 (q) ppm. GC/MS: 118 (20%, M$^+$), 87 (10%), 59 (100%), 56 (20%), 43 (77%), 42 (26%), 30 (74%), 28 (21%).

Example 3. Preparation of Nitroso-Emu

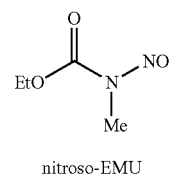

nitroso-EMU

H$_3$PO$_4$ 50% in water (683 g, 3.44 mol) is added to ethyl methylcarbamate (412 g, 4 mol) at 10-20° C. under stirring (300 rpm). To the colorless 2-phase mixture is added NaNO$_2$ 30% in water (1123 g, 4.9 mol) at 10-15° C. over 6 h. Nitrous gases are formed after 50% addition which are absorbed in two washing bottles containing 10% (NH$_4$)$_2$SO$_4$ in water. The orange solution is stirred for 17 h at 25° C. and is purged with nitrogen until the remaining nitrous gases are removed. Stirring is stopped and a sample is taken from the orange organic layer for analytical analysis which shows a 76-82% conversion according to GCMS and NMR. The reaction mixture is extracted twice with toluene (2×1 l) to give 2.5 l of a clear light orange solution which is used as such in the cyclopropanation step. Analytical data of the organic layer before toluene addition: $^1$H-NMR (CDCl$_3$, 400 MHz): 4.55 (q, 2H), 3.2 (s, 3H), 1.5 (t, 3H) ppm. $^{13}$C-NMR (CDCl$_3$, 400 MHz): 153.8 (s), 64.5 (t), 28.0 (q), 14.25 (q) ppm. GC/MS: 132 (6%, M$^+$), 87 (10%), 60 (48%), 58 (20%), 56 (14%), 43 (83%), 30 (56%), 29 (100%).

Example 4. Preparation of Δ-Myrcene 1 and Δ$_2$-Myrcene 2

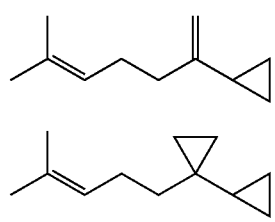

N-Methyl-N-nitroso urea 1.35 M in THF (810 ml, 1.1 mol, from example 1) is added at 0° C. to myrcene 94% tech. (100 g, 0.69 mol) and 40% aqueous KOH (300 ml) under strong stirring. After the addition of 20 ml MNU in THF, palladium acetylacetonate (0.45 g, 0.2%) pre-dissolved in dichloromethane (20 ml) is added. The remaining 790 ml MNU in THF are added within 5.5 h at 0° C. After another 1.5 h at 0° C. complete conversion is detected by GC which shows 85% Δ-Myrcene and 11% Δ$_2$-Myrcene (rpa).

Acetic acid (300 ml) is added within 3 h at 0-5° C., then 2M HCl (500 ml) at 25° C. After phase separation the water phase is extracted with 2×400 ml tert-butyl methyl ether. The combined organic phases are washed with 2×500 ml water, 500 ml 10% NaOH and 500 ml NaCl, are dried over MgSO$_4$, filtered and concentrated under reduced pressure. To the remaining yellow liquid (109 g) paraffin oil (20 g) and K$_2$CO$_3$ (0.5 g) are added. Distillation over a 30 cm steel coil column at 40-50 mbar gives 1 g Myrcene (1% corr) at 75° C., 81.2 g Δ-Myrcene 1 (78% corr) at 93-98° C. and 9.3 g Δ$_2$-Myrcene 2 (8% corr) at 95-105° C. The fractions are pooled to give 70.5 g Δ-Myrcene of 100% purity and 5.3 g Δ$_2$-Myrcene of 87% purity.

Analytical data of Δ-Myrcene 1: $^1$H-NMR (CDCl$_3$, 400 MHz): 5.1 (m, 1H), 4.6 (2H), 2.15 (2H), 2.0 (1H), 1.7 (s, 3H), 1.6 (s, 3H), 1.3 (1H), 0.6 (2H), 0.4 (2H) ppm. $^{13}$C-NMR (CDCl$_3$, 400 MHz): 150.9 (s), 135.5 (s), 124.2 (d), 106.0 (t), 35.9 (t), 26.8 (t), 25.6 (q), 17.7 (q), 16.1 (d), 6.95 (t) ppm. GC/MS: 150 (1%, M$^+$), 135 (6%, [M−15]$^+$), 121 (3%), 107 (88%), 93 (11%), 91 (18%), 79 (62%), 77 (11%), 69 (82%), 67 (26%), 53 (18%), 41 (100%). IR (film): 3081 (m), 3003 (w), 2968 (m), 2915 (m), 2856 (m), 1642 (m), 1440 (m), 1376 (m), 1239 (w), 1211 (w), 1172 (w), 1102 (m), 1047 (m), 1018 (m), 984 (w), 958 (w), 937 (w), 875 (s), 820 (m), 627 (m). Anal. calcd. for C$_{11}$H$_{18}$: C, 87.93; H, 12.07. Found: C, 87.22; H, 12.00.

Analytical data of Δ$_2$-Myrcene 2: $^1$H-NMR (CDCl$_3$, 400 MHz): 5.1 (m, 1H), 2.15 (m, 2H), 1.7 (s, 3H), 1.6 (s, 3H), 1.35 (m, 2H), 1.15 (m, 1H), 0.3 (2H), 0.1 (4H), −0.1 (m, 2H) ppm. $^{13}$C-NMR (CDCl$_3$, 400 MHz): 130.9 (s), 125.1 (d), 40.0 (t), 25.7 (q), 25.6 (t), 20.3 (s), 17.5 (q), 14.3 (d), 9.2 (2C, t), 1.9 (2C, t) ppm. GC/MS: 149 (12%, [M−15]$^+$), 136 (11%), 121 (38%), 107 (17%), 95 (13%), 93 (46%), 91 (15%), 81 (17%), 79 (47%), 77 (15%), 69 (100%), 67 (47%), 65 (10%), 55 (30%), 53 (23%), 41 (100%), 39 (26%). IR (film): 3075 (m), 3002 (m), 2968 (m), 2914 (m), 2854 (m), 2730 (w), 2053 (w), 1642 (w), 1450 (m), 1376 (m), 1244 (w), 1107 (m), 1097 (m), 1045 (m), 1011 (s), 984 (w), 952 (m), 884 (m), 858 (w), 819 (m), 742 (w), 665 (w), 631 (w).

Example 5. Cyclopropanation of Myrcene with Mnu in Various Solvents

| run | scale | equiv MNU | solvent | catalyst | time | % β-E-Farnesene | % monocyclo-propane 1 | % biscyclo-propane 2 |
|---|---|---|---|---|---|---|---|---|
| 1$^a$ | 20 g | 1.7 | NMP$^b$ | Pd(OAc)$_2$ | 1 h | 4% | 82% | 10% |
| 3 | 5 g | 1.3 | DME | Pd(acac)$_2$ | 2 h | 7% | 85% | 7% |
| 4 | 2 g | 1.5 | DMIS | Pd(acac)$_2$ | 2 h | 7% | 80% | 6% |
| 5 | 5 g | 1.5 | THF | Pd(acac)$_2$ | 2 h | 8% | 84% | 7% |

Conditions: Addition of MNU in different solvents to Myrcene, 0.2% Pd(II)-catalyst and 40% aqueous KOH at 0-5° C. under stirring until maximum conversion of Myrcene to monocyclopropane 1 is reached.
$^a$ 0.5 equiv of internal standard tetradecane.
$^b$ gas bubbles in MNU/NMP dropping funnel.

Example 6. Cyclopropanation of Myrcene 1 with of N-Nitroso-Dimethylurethane

Pd(acac)$_2$ (5.6 mg, 0.05%) in toluene (1 ml) is added at 0-5° C. to a stirred mixture of myrcene 85% tech. (5 g, 31 mmol) in toluene (25 ml) and 40% aqueous KOH (15 ml). N-Nitroso-dimethylurethane 1.8 M in toluene (30 ml, 55 mmol, from example 2) is added at 0-5° C. over 1 h. The strong yellow reaction mixture shows after 1 h at 0-5° C. a 87% conversion and after 18 h at room temperature a 96% conversion to Δ-Myrcene (77%) and Δ$_2$-Myrcene (7%) according to GC. The organic phase is separated and the aqueous phase extracted with toluene (50 ml). Both organic phases are washed with acetic acid (25 ml), water (25 ml), 10% NaOH (25 ml) and water (3×25 ml). The organic phases are combined, dried over MgSO$_4$, filtered and concentrated under reduced pressure. The remaining yellow oil (4.2 g) is bulb-to-bulb distilled at 100-120° C./20 mbar giving 2.9 g (61%) of a product mixture containing 2% Myrcene, 84% Δ-Myrcene 1 and 8% Δ$_2$-Myrcene 2. The analytical data of these components are identical with the ones obtained in example 4.

Example 7. Cyclopropanation of myrcene 1 with n-nitroso-3-methylaminoisobutyl methyl Ketone (nmk)

Pd(acac)$_2$ (21 mg, 0.5%) is added at 0-5° C. to a stirred mixture of freshly distilled myrcene (2 g, 15 mmol) and 40% aqueous KOH (5 ml). NMK (4.6 g, 29 mmol), prepared as described in WO 2013110932, is added dropwise at 0-5° C. within 0.5 h. After another hour at 0-5° C. the brown suspension is stirred for another 2 h at 25° C. (87% conversion according to GC). After 21 h the mixture is quenched with acetic acid (10 ml) and the biphasic mixture is extracted with tert-butyl methyl ether (2×50 ml). The organic layers are washed with water (25 ml), 10% NaOH (25 ml) and water (25 ml). Both organic phases are combined, dried over MgSO$_4$, filtered and concentrated under reduced pressure. The remaining yellow oil (4.1 g) is bulb-to-bulb distilled at 50-150° C./10 mbar giving 1 g mesityl oxide (35%), 0.26 g myrcene (14%), 1.4 g Δ-Myrcene 1 (69%) and 0.07 g Δ$_2$-Myrcene 2 (3%). The analytical data of the main components are identical with the ones obtained in example 4.

Example 8. Preparation of Δ-Ocimene 3 from Ocimene

3

Prepared as described in example 5 from MNU 1.35 M in THF (38 ml, 51 mmol), E/Z-Ocimene (3 g, 22 mmol), 40% aqueous KOH (10 ml) and palladium acetate (15 mg, 0.3%) pre-dissolved in THF (1.5 ml). After 1 h at 0° C. and 4 h at 25° C. GC shows 94% Δ-Ocimene and 6% Ocimene (rpa). Work-up gives 3.1 g of crude Δ-Ocimene 3 (E/Z 3:1) as crude yellowish oil.

Analytical data: $^1$H-NMR (CDCl$_3$, 400 MHz): 5.2 and 5.1 (2H), 2.85 and 2.7 (1H, CH$_2$), 1.7 (1H), 1.7 (s, 3H), 1.65 (s, 3H), 1.55 and 1.4 (2 s, E/Z, 3H), 0.45 (2H) ppm. $^{13}$C-NMR (CDCl$_3$, 400 MHz, E-isomer and selected signals of the Z-isomer): 135.4 (s), 131.3 (s), 123.3 (d), 121.9 (d), 27.0 (t), 25.7 (q), 25.675 (q), 18.7 (d), 17.7 (q), 13.8 (q), 4.2 (t) ppm. 26.6 (t, Z), 18.9 (q, Z), 4.0 (t, Z). GC/MS (E/Z overlap): 150 (14%, M+), 135 (43%, [M-15]+), 121 (17%), 109 (16%), 107 (100%), 105 (39%), 94 (17%), 93 (57%), 91 (67%), 82 (36%), 81 (40%), 79 (75%), 77 (39%), 69 (22%), 67 (56%), 65 (15%), 55 (24%), 53 (27%), 41 (65%), 39 (43%).

Example 9. Preparation of e-ΔFarnesene 4 and e-Δ₂-Farnesene 5 using MNU in THF

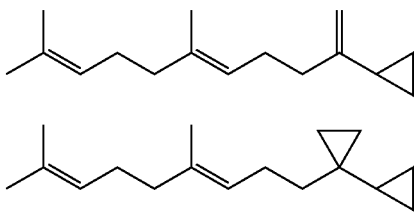

N-Methyl-N-nitroso urea 1.35 M in THF (136 ml, 184 mmol) is added dropwise at 0° C. to a rapidly stirred mixture of β-E-Farnesene (CAS 18794-84-8) (25 g, 122 mmol) and aqueous KOH (50 ml, 40%) at 0-5° C. After the addition of 4 ml of the MNU solution, Pd(acac)₂ (7.4 mg, 0.024 mmol, 0.02%) pre-dissolved in 0.5 ml dichloromethane is added. The remaining MNU solution is added over 4 h at 0-5° C. A GC at this stage showed 28% unconverted E-β-Farnesene, 65% monocyclopropane 4 and 3% biscyclopropane 5. After 16 h at 25° C. acetic acid (100 ml) is added at 0-5° C., then tert-butyl methyl ether (250 ml). After phase separation the organic phase is washed with 2M HCl (250 ml) and the aqueous phase extracted with tert-butyl methyl ether (250 ml). The combined organic layers are washed with water (2×100 ml), aqueous 10% NaOH (2×100 ml) and water (2×100 ml), dried over MgSO4, filtered and concentrated to give 26.9 g of a slightly yellow liquid which contains 9% E-β-Farnesene, 82% monocyclopropane 4 and 6% biscyclopropane 5.

Example 10. Distillative Purification of E-Δ-Farnesene 4 and E-Δ₂-Farnesene 5 Prepared from MNU in NMP Under similar conditions as described in example 9, E-β-Farnesene (193.4 g, 0.945 mol) is cyclopropanated in the presence of Pd(acac)₂ (0.58 g, 1.9 mmol, 0.2%) pre-dissolved in dichloromethane (40 ml) and 40% KOH (400 ml) with MNU (1.3 mol) in 800 ml NMP (under slight but constant gas evolution in the MNU/NMP dropping funnel). Work-up gives a slightly yellow liquid (202 g) which contains 3% E-β-Farnesene, 75% monocyclopropane 4 and 12% biscyclopropane 5. Addition of 1 g K₂CO₃ (1 g) and distillation over a 30 cm steel coil column at 40-60 mbar gives 6.3 g E-β-Farnesene (3% corr) at 125-135° C., 147 g monocyclopropane 4 (68% corr) at 135-145° C., 20.3 g biscyclopropane 5 (10% corr) at 145-155° C. and 18 g of residue. The fractions are pooled to give 92 g monocyclopropane 4 of 100% purity and 10 g biscyclopropane 5 of 93% purity as colorless liquids.

Analytical Data of E-Δ-Farnesene 4:
¹H-NMR (CDCl₃, 400 MHz): 5.1 (2 m, 2H), 4.6 (2H), 2.2 (2H), 2.1 (4H), 2.0 (2H), 1.7 (s, 3H), 1.6 (2 s, 6H), 1.3 (1H), 0.6 (2H), 0.45 (2H) ppm. ¹³C-NMR (CDCl₃, 400 MHz): 150.9 (s), 135.1 (s), 131.2 (s), 124.4 (d), 124.1 (d), 106.0 (t), 39.7 (t), 35.9 (t), 26.7 (t), 25.7 (q), 17.7 (q), 16.0 (d), 6.0 (t) ppm. GC/MS: 218 (2%, M+), 203 (5%, [M-15]+), 175 (11%), 147 (31%), 134 (15%), 133 (20%), 121 (12%), 107 (55%), 95 (16%), 93 (30%), 91 (20%), 82 (11%), 81 (33%), 79 (42%), 69 (100%), 67 (22%), 55 (20%), 53 (21%), 41 (75%). IR (film): 3081 (w), 2967 (m), 2915 (m), 2854 (m), 1642 (m), 1439 (m), 1377 (m), 1107 (w), 1047 (w), 1018 (m), 875 (s), 819 (m), 629 (w). Anal. calcd. for C₁₆H₂₆: C, 88.00; H, 12.00. Found: C, 87.80; H, 12.01.

Analytical Data of E-Δ₂-Farnesene 5:
¹H-NMR (CDCl₃, 400 MHz): 5.15 (2 m, 2H), 2.25 (m, 2H), 2.05 (m, 2H), 2.0 (m, 2H), 1.7 (s, 3H), 1.65 (2 s, 6H), 1.4 (m, 2H), 1.05 (m, 1H), 0.3 (m, 2H), 0.15 (4H), -0.05 (m, 2H) ppm. ¹³C-NMR (CDCl₃, 400 MHz): 134.5 (s), 131.2 (s), 124.9 (d), 124.4 (d), 40.0 (t), 39.7 (t), 26.7 (t), 25.7 (q), 25.5 (t), 20.3 (s), 17.6 (q), 15.9 (q), 14.3 (d), 9.2 (2C, t), 1.9 (2C, t) ppm. GC/MS: 232 (0.2%, M+), 217 (3%, [M-15]+), 204 (4%), 189 (10%), 161 (8%), 147 (12%), 121 (22%), 107 (20%), 95 (27%), 93 (31%), 91 (13%), 81 (42%), 79 (30%), 69 (100%), 67 (33%), 55 (24%), 53 (16%), 41 (67%). IR (film): 3075 (w), 3001 (w), 2967 (m), 2913 (m), 2849 (m), 1669 (w), 1448 (m), 1377 (m), 1107 (m), 1045 (m), 1011 (s), 984 (w), 952 (w), 884 (w), 819 (m), 740 (w), 664 (w). Anal. calcd. for C₁₇H₂₈: C, 87.86; H, 12.14. Found: C, 87.59; H, 12.09.

Example 11. Preparation of a E-α-Δ-Farnesene 6 mixture from E-α,β-Farnesene

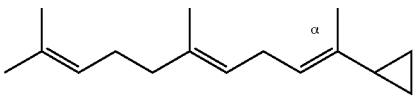

Prepared as described in example 9 from N-methyl-N-nitroso urea 1.35 M in THF (10 ml, 13.5 mmol), E-α,β-Farnesene (1 g, 5 mmol, purity Zα/β/Eα 17:50:26, GC, rpa), aqueous KOH (2.5 ml, 40%) and Pd(OAc)₂ (3.3 mg, 0.015 mmol, 0.3%) pre-dissolved in 0.75 ml THF. Work-up and bulb-to-bulb distillation gives 0.76 g of a colorless liquid which contains E-β-Farnesene 4 (46%), E-α-Δ-Farnesene 6 (39%) and 10% unconverted farnesenes. GC/MS: 218 (0.2%, M+), 203 (3%, [M-15]+), 175 (4%), 149 (8%), 147 (9%), 133 (13%), 123 (50%), 121 (22%), 119 (15%), 107 (70%), 105 (30%), 95 (35%), 93 (90%), 91 (57%), 81 (80%), 79 (55%), 77 (33%), 69 (95%), 67 (27%), 55 (36%), 53 (21%), 41 (75%).

Example 12. Ethyl 8-Cyclopropyloctanoate 7

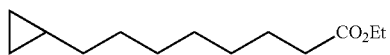

Prepared as described in example 4 from N-methyl-N-nitroso urea 1.35 M in THF (31 ml, 42 mmol), ethyl decenoate (5 g, 25 mmol), 40% aqueous KOH (10 ml) and palladium acetylacetonate (15 mg, 0.2%) pre-dissolved in dichloromethane (1 ml). Work-up gives 4.5 g (88%) of crude ethyl 8-cyclopropyloctanoate 7 as slightly yellow liquid.

Analytical data: $^1$H-NMR (CDCl$_3$, 400 MHz): 4.15 (q, 2H), 2.3 (t, 2H), 1.6 (m, 2H), 1.3-1.5 (8H), 1.3 (t, 3H), 1.2 (dt, 2H), 0.65 (m, 1H), 0.4 (m, 2H), 0.0 (m, 2H) ppm. $^{13}$C-NMR (CDCl$_3$, 400 MHz): 134.5 (s), 131.2 (s), 124.9 (d), 124.4 (d), 40.0 (t), 39.7 (t), 26.7 (t), 25.7 (q), 25.5 (t), 20.3 (s), 17.6 (q), 15.9 (q), 14.3 (d), 9.2 (2C, t), 1.9 (2C, t) ppm. GC/MS: 212 (0.2%, M$^+$), 197 (0.2%, [M−15]$^+$), 169 (1%), 167 (2%), 166 (3%), 149 (3%), 138 (8%), 124 (15%), 123 (8%), 110 (7%), 101 (37%), 96 (30%), 73 (20%), 69 (30%), 67 (20%), 61 (15%), 60 (17%), 55 (100%), 41 (50%). IR (film): 3076 (w), 2997 (w), 2923 (m), 2857 (m), 1735 (s), 1463 (m), 1427 (w), 1372 (m), 1348 (w), 1301 (w), 1247 (w), 1175 (m) 1115 (m), 1097 (m), 1035 (m), 1014 (m), 946 (w), 856 (w), 820 (w), 723 (w), 629 (w).

Example 13. 3-cyclopropyl-1-(spiro[4.5]Dec-7-en-7-yl)propan-1-one and 3-cyclopropyl-1-(spiro[4.5]Dec-6-en-7-yl)propan-1-one 8

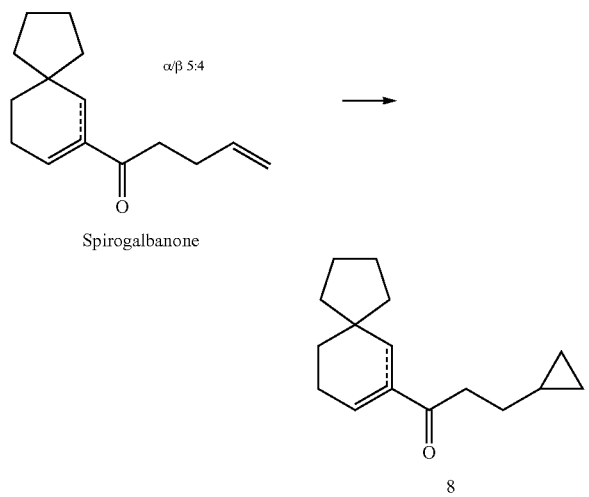

Prepared as described in example 4 from N-methyl-N-nitroso urea 1.35 M in THF (18 ml, 24 mmol), Spirogalbanone (3 g, 25 mmol, EP 913383, priority to Givaudan 29.10.1997), 40% aqueous KOH (10 ml) and palladium acetylacetonate (8.4 mg, 0.2%) pre-dissolved in dichloromethane (0.5 ml). Work-up gives 3.2 g (quant) of crude cyclopropane 8 as a slightly yellow liquid. Purity: 98%, α/β-isomer ratio 58:42 (GC).

Analytical data: $^1$H-NMR (CDCl$_3$, 400 MHz): 6.9 and 6.6 (1H, α- and β-isomer), 2.75 (t, 2H), 2.25, 2.15 2.1 and 1.7 (4H), 1.3-1.7 (12H), 0.65 (1H), 0.35 (m, 2H), 0.0 (2H) ppm. $^{13}$C-NMR (CDCl$_3$, 400 MHz): 201.9 and 201.7 (2 s, CO), 148.3 and 139.2 (2 d), 138.8 and 136.8 (2 s), 44.2 and 40.6 (2 s), 40.1, 38.13, 37.2, 37.1, 35.4, 34.4, 32.85, 30.2, 30.1, 24.8, 24.65, 24.4, 23.5, 20.1 (7×2 t), 10.7 (2 d), 4.55 and 4.5 (2 t) ppm. GC/MS (f-isomer, t$_R$=9.84 min): 232 (24%, M$^+$), 217 (2%, [M−15]$^+$), 204 (10%), 203 (13%), 189 (11%), 177 (15%), 176 (54%), 175 (28%), 149 (13%), 148 (21%), 147 (27%), 136 (10%), 135 (56%), 134 (24%), 133 (34%), 131 (12%), 121 (27%), 120 (15%), 119 (21%), 117 (14%), 107 (43%), 105 (39%), 93 (100%), 91 (98%), 81 (38%), 79 (78%), 77 (63%), 69 (18%), 67 (63%), 65 (24%), 55 (71%), 53 (30%), 43 (18%), 41 (77%), 39 (29%). GC/MS (α-isomer, t$_R$=9.96 min): 232 (38%, M$^+$), 217 (3%, [M−15]$^+$), 204 (16%), 203 (25%), 178 (8%), 175 (6%), 164 (12%), 163 (100%), 161 (9%), 147 (10%), 135 (27%), 133 (19%), 121 (22%), 119 (14%), 117 (13%), 109 (18%), 107 (58%), 105 (26%), 95 (37%), 93 (88%), 91 (73%), 81 (57%), 79 (79%), 77 (47%), 69 (27%), 67 (80%), 65 (21%), 57 (10%), 55 (78%), 53 (62%), 43 (17%), 41 (80%), 39 (30%), 29 (16%). IR (film): 3075 (w), 2998 (w), 2929 (m), 1664 (s), 1636 (w), 1446 (w), 1379 (w), 1340 (w), 1271 (w), 1212 (w), 1189 (m), 1103 (w), 1043 (w), 1013 (m), 942 (w), 819 (w), 753 (w), 697 (w).

Example 14. 1-cyclopropyl-3-methylbenzene 9

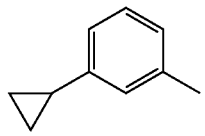

Prepared as described in example 4 from N-methyl-N-nitroso urea 1.35 M in THF (19 ml, 25.6 mmol), 1-methyl-3-vinylbenzene (2 g, 17 mmol), 40% aqueous KOH (10 ml) and palladium acetylacetonate (10.3 mg, 0.2%) pre-dissolved in dichloromethane (0.5 ml). Work-up gives 2.2 g (quant) of crude 1-cyclopropyl-3-methylbenzene 9 as a slightly yellow liquid.

Analytical data: $^1$H-NMR (CDCl$_3$, 400 MHz): 7.15 (dd, 1H), 6.95 (d, 1H), 6.85 (2H), 2.3 (s, 3H), 1.85 (m, 1H), 0.9 (m, 2H), 0.65 (m, 2H) ppm. $^{13}$C-NMR (CDCl$_3$, 400 MHz): 143.9 (s), 137.8 (s), 128.2 (d), 126.5 (d), 126.2 (d), 122.7 (d), 21.4 (q), 15.3 (d), 9.1 (2C, t) ppm. GC/MS: 132 (40%, M$^+$), 131 (17%), 118 (10%), 117 (100%), 116 (15%), 115 (44%), 105 (8%), 103 (6%), 91 (28%), 77 (12%), 65 (12%), 63 (10%), 51 (11%), 39 (16%). IR (film): 3081 (w), 3008 (m), 2919 (w), 1607 (m), 1589 (w), 1491 (m), 1462 (m), 1430 (w), 1378 (w), 1242 (w), 1170 (w), 1090 (w), 1044 (m), 1018 (m), 924 (m), 865 (w), 812 (m), 774 (s), 696 (s).

Example 15. (E)-2-methyl-6-methylenenona-2,7-diene 10 (e-homomyrcene)

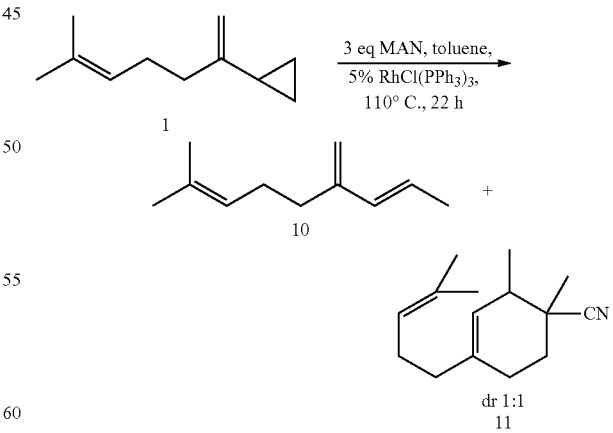

Methacrylonitrile (1.3 g, 19 mmol) and Wilkinson's catalyst RhCl(PPh$_3$)$_3$ (0.3 g, 0.3 mmol) are added to Δ-myrcene 1 (1 g, 6.7 mmol) in toluene (15 ml) under nitrogen and stirring. The mixture is heated 22 h at reflux, cooled to 25° C. and filtered over silica gel. After addition of water (50 ml)

and phase separation the aqueous phase is extracted with toluene. The combined organic layers are dried over NaSO₄, filtered and concentrated under reduced pressure to give 1.25 g of a clear liquid. GCMS reveals 63% E-Homomyrcene 10, 26% isomers (M 150) and 11% Diels-Alder adducts 11. Bulb-to-bulb distillation at 40° C./0.1 mbar gives 0.22 g (22%) of E-homomyrcene 10 and 0.55 g of a residue. The analytical data of E-Homomyrcene 10 and of the Diels-Alder adducts 11 were identical with the ones described in the literature (*Tetrahedron* 65, 10495, 2009 and references therein).

Example 15. 1-((1SR,2RS)-1,2-dimethyl-4-(4-methylpent-3-EN-1-yl)cyclohex-3-en-1-yl)ethanone 12 (pseudo-georgywood)

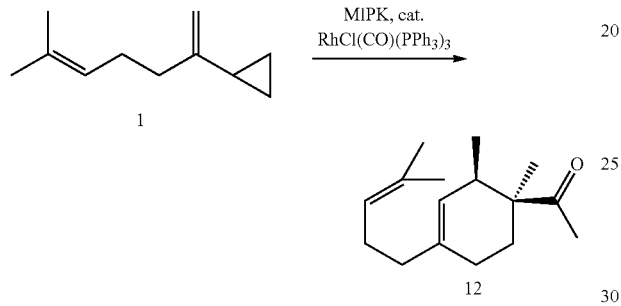

3-Methylbutan-2-one (3.7 g, 13 mmol) and Wilkinson's catalyst RhCl(PPh₃)₃ (0.6 g, 0.7 mmol) are added to Δ-myrcene 1 (2 g, 13.3 mmol) in toluene (30 ml) under nitrogen and stirring. The mixture is heated 41 h at reflux, cooled to 25° C. and filtered over silica gel. After addition of water (50 ml) and phase separation the aqueous phase is extracted with toluene. The combined organic layers are dried over NaSO₄, filtered and concentrated under reduced pressure to give 2.7 g of a clear liquid. Bulb-to-bulb distillation at 100-160° C./0.05 mbar gives 1.31 g (42%) of a 3:1 isomer mixture containing Georgywood 12 as main product, whose analytical data were identical with the ones described in the literature, see for example *Tetrahedron: Asymmetry* 15, 3967 (2004).

Example 16. Preparation of Δ-Myrcenol 13

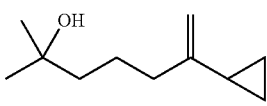

Prepared as described in example 4 from N-methyl-N-nitroso urea 1.35 M in THF (72 ml, 97 mmol), myrcenol (10 g, 65 mmol, *Chemistry Letters* 15, 157-160, 1986 and references therein), aqueous KOH (32 ml, 40%) and Pd(acac)₂ (20 mg, 0.065 mmol, 0.2%) pre-dissolved in 2.6 ml THF. After 1 h at 0° C. quantitative conversion is detected by GC. Work-up gives 10.7 g of crude 13 as a yellowish oil which is purified by flash chromatography over silica gel with eluent hexane/tert-butyl methyl ether 1:1. Evaporation of the solvents gives 9.45 g (87%) of 13 as a colorless oil. 4.2 g of this material were further purified by bulb-to-bulb distillation at 60° C./0.03 mbar and gave 4 g of olfactorily pure Δ-Myrcenol 13. Olfactory profile: floral, rosy, slightly aldehydic. Purity: 96%. According to NMR and GC this material contains 4% of Δ₂-Myrcenol 14.

Analytical Data of 13: ¹H-NMR (CDCl₃, 400 MHz): 4.6 (m, 2H), 2.05 (m, 2H), 1.6 (m, 2H), 1.5 (m, 2H), 1.3 (m, 2H), 1.2 (6H, s), 0.65 (m, 2H), 0.43 (m, 2H) ppm. ¹³C-NMR (CDCl₃, 400 MHz): 150.9 (s), 106.05 (t), 71.0 (s), 43.6 (t), 36.5 (t), 29.25 (q), 22.85 (t), 15.93 (d), 6.1 (t). GC/MS: 150 (8%, [M−18]⁺), 135 (15%, [M−18-15]⁺), 122 (2%), 121 (4%), 109 (11%), 107 (24%), 95 (25%), 94 (41%), 93 (19%), 91 (8%), 82 (18%), 79 (100%), 77 (10%), 69 (14%), 67 (41%), 59 (60%), 43 (28%), 41 (27%).

GCMS of Δ₂-Myrcenol 14: 149 (16%, [M−18-15]⁺), 135 (10%), 121 (31%), 109 (22%), 108 (30%), 107 (24%), 95 (20%), 94 (15%), 93 (88%), 91 (18%), 81 (42%), 80 (58%), 79 (100%), 77 (10%), 69 (24%), 67 (44%), 59 (67%), 43 (34%), 41 (49%).

Example 17. Preparation of Toscanol 16

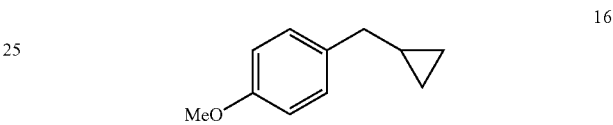

Pd(acac)₂ (0.15 g, 0.5 mmol, 0.05 mol %) is added at 0-5° C. to a stirred (300 rpm) mixture of estragol (148 g, 1 mol) in toluene (1 l) and 40% aqueous KOH (0.5 l). Nitroso-EMU 1.63 M in toluene (1.25 l, 2 mol, prepared as described in example 3) is added at 0-5° C. over 6 h. The bright yellow reaction mixture is stirred for another hour at 0-5° C., then 17 h at room temperature. GC-analysis shows a quantitative conversion to Toscanol. The organic phase is separated and the aqueous phase extracted with toluene (1 l). The organic phases are washed with water (1 l), 10% acetic acid (1 l), water (1 l), 10% NaOH (1 l) and water (2×1 l). Both organic phases are combined, dried over MgSO₄, filtered and concentrated under reduced pressure. The remaining yellow oil (173.7 g) is short-path-distilled at 70-150° C./0.07 mbar giving 159 g (98% corr) of Toscanol 16 with a purity of 84-100% (over all fractions). The NMR data are identical with the ones reported in the literature for this compound, e.g. in S.-K. Tiana et al., *Adv. Synth. & Cat.* 353, 1980-1984 (2011).

GCMS of Toscanol 16: 162 (22%, M⁺), 147 (8%), 134 (23%), 121 (100%), 119 (11%), 91 (18%), 78 (8%), 77 (10%), 65 (7%).

The invention claimed is:

1. A process of ring formation across a carbon-carbon multiple bond, the process comprising the steps of reacting a N-alkyl-N-nitroso compound with a substrate bearing a carbon-carbon multiple bond, wherein the N-alkyl-N-nitroso compound has been generated in-situ, and the generated N-alkyl-N-nitroso compound is reacted with the substrate without being first isolated.

2. The process according to claim 1, wherein the N-alkyl-N-nitroso compound is an organic solution of N-alkyl-N-nitroso urea, and wherein the N-alkyl-N-nitroso urea is reacted with the substrate without being first isolated in solid form.

3. The process according to claim 1, wherein the N-alkyl-N-nitroso compound is a N-methyl-N-nitroso compound (MNC).

4. The process according to claim 1, wherein the N-alkyl-N-nitroso compound is selected from the group consisting of N-methyl-N-nitroso-urea (MNU), N-methyl-N-nitroso-p-toluenesulfonamide, N-nitroso-dimethylurethane, nitroso-EMU and N-nitroso-β-methylaminoisobutyl methyl ketone (NMK).

5. The process according to claim 1, wherein the N-alkyl-N-nitroso compound is generated in-situ from a mixture of a HNRR' compound, water, NaNO$_2$ and an acid, before partitioning into an organic solvent to form an organic solution of N-alkyl-N-nitroso compound.

6. The process according to claim 5 wherein the N-alkyl-N-nitro compound is formed in-situ from a N-alkylamine.

7. The process according to claim 1, wherein a biphasic mixture is formed with the N-alkylN-nitroso compound in an organic layer.

8. The process according to claim 1, wherein the N-alkyl-N-nitroso compound in liquid phase is separated from an aqueous phase in a phase separation step, before being reacted with the substrate bearing a carbon-carbon multiple bond.

9. The process according to claim 1, wherein the N-alkyl-N-nitroso compound is reacted with the substrate bearing a carbon-carbon multiple bond in the presence of an aqueous base and a catalyst.

10. The process of converting a carbon-carbon double bond to a cyclopropane ring according to claim 1.

11. A process of converting a carbon-carbon double bond to a cyclopropane ring comprising the steps of:
   I) synthesis of a N-alkyl-N-nitroso compound in liquid phase,
   II) separation of an organic N-alkyl-N-nitroso compound-containing liquid phase from an aqueous phase, and
   III) transferring the N-alkyl-N-nitroso compound in the organic liquid phase into a mixture comprising an alkene substrate, thereby to cyclopropanate the alkene substrate, wherein the alkene substrate is a terminal (monosubstituted) isoprenoid alkene.

12. The process according to claim 6, wherein the N-alkylamine is methyl, ethyl, propyl or higher alkyl amine, which may be substituted or unsubstituted and linear or branched.

13. The process according to claim 3, wherein a liquid phase comprises an organic solvent for the MNC that is selected from the group consisting of ethers and toluene.

14. The process according to claim 13 wherein the ether is selected from the group consisting of tetrahydrofurane, dimethoxyethane, dioxane and dimethylisosorbide.

15. The process according to claim 9, wherein the aqueous base is selected from the group consisting of alkali hydroxides.

16. The process according to claim 9, wherein the catalyst is a transition metal catalyst, optionally a palladium catalyst, further optionally Pd(acac)$_2$, Pd(OAc)$_2$ or PdCl$_2$ catalysts.

17. The process according to claim 1, which is conducted in flow mode.

18. The process according to claim 1, wherein the substrate bearing a carbon-carbon multiple bond is a terminal (monosubstituted) alkene.

19. The process according to claim 1, wherein the substrate bearing a carbon-carbon multiple bond is a compound of the formulae

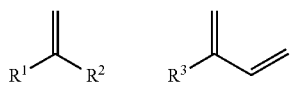

wherein R$^1$ and R$^2$ may, independently of each other, be hydrogen, alkyl, alkylidene, or aryl, which may be branched or unbranched and substituted or unsubstituted;

and R$^3$ may be an alkyl, alkylidene, or aryl, which may be branched or unbranched and substituted or unsubstituted.

20. The process according to claim 18, wherein the substrates are isoprenoids.

21. A compound according to the formula

IIIa

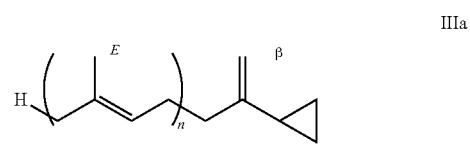

in which n=1 or 3.

22. A compound according to claim 21 comprising

1

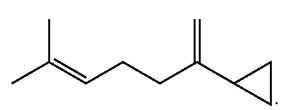

* * * * *